(12) United States Patent
Endou et al.

(10) Patent No.: US 6,673,898 B1
(45) Date of Patent: Jan. 6, 2004

(54) PLACENTAL ORGANIC ANION TRANSPORTER

(75) Inventors: Hitoshi Endou, Sagamihara (JP); Takashi Sekine, Tachikawa (JP); Seok Ho Cha, Mitaka (JP)

(73) Assignee: Japan Science and Technology Corporation, Saitama-ken (JP)

( * ) Notice: Subject to any disclaimer, the term of this patent is extended or adjusted under 35 U.S.C. 154(b) by 21 days.

(21) Appl. No.: 09/786,261

(22) PCT Filed: Jun. 15, 2000

(86) PCT No.: PCT/JP00/03878

§ 371 (c)(1),
(2), (4) Date: Jun. 7, 2001

(87) PCT Pub. No.: WO01/02562

PCT Pub. Date: Nov. 1, 2001

(30) Foreign Application Priority Data

Jul. 1, 1999 (JP) .............................. 11-187244

(51) Int. Cl.$^7$ .......................... C07K 14/00; C12N 9/00
(52) U.S. Cl. ..................................... 530/350; 435/183
(58) Field of Search .......................... 435/252.3, 320.1, 435/325, 254.11, 69.1, 183; 530/350

(56) References Cited

FOREIGN PATENT DOCUMENTS

| WO | WO98/53064 A1 | 11/1998 |
| WO | WO99/13072 | 3/1999 |
| WO | WO 01/49728 A | 7/2001 |
| WO | WO 01/62923 A | 8/2001 |

OTHER PUBLICATIONS

Bisson, et al, 1993, Crit Rev Biochem Mol Biol, 28:259–308.*
Liang, H., et al, 1998, Mol. Cell. Biol. 18(2):926–935.*
Race, et al, 1999, Biochem. Biophys. Res. Comm., 255: 508–514.*
M. Hosoyhamada et al., *American Journal of Physiology*, vol. 276, No. 1, Part 2, pp. F122–F128 (1999).
J. Race et al., *Biochemical and Biophysical Research Communications*, 255(2):508–514 (1999).
Database EMBL Online, AC H12876, XP002188136 (1995).
Database EMBL Online, AC N54154, XP002188137 (1996).
Van Der et al., *Placenta*, 15(3):279–289 (1994).
H. Cha Seok et al., *Journal of Biological Chemistry*, 275(6):4507–4512 (2000).
Sekine T., et al. "Molecular cloning and characterization of multispecific organic anion transporter 4 expressed in the placenta"Japanese Journal of Pharmacology (Mar. 2000), vol. 82, suppl. 1, p. 114P.
Sekine T., et al. "Molecular identification of an organic anion transporter (OAT) family and its role in the transmemberane trasnport of anionic drugs", Japanese Journal of Pharmacology (Mar. 2000), vol. 82, suppl. 1, p. 5P.
Sekine T., et al., "Expression cloning and characterization of a novel multispecific organic anion transporter", Journal of Biological Chemistry (1997), vol. 272, No. 30, p. 18526–18529.
Sekine T., et al. "Identification of multispecific organic anion transporter 2 expressed predominantly in the liver", FEBS Letters (1998), vol. 429, p. 179–182.
Kusuhara H., et al., "Molecular cloning and characterization of a new multispecific organic anion transporter from rat brain", Journal of Biological Chemistry (May 1999), vol. 274, No. 19, p. 13675–13680.
Endou H., et al. "Recent advances in molecular mechanisms of nephrotoxicity", Toxicology Letters (1998), vol. 102–103, p. 29–33.
Hillier L., et al. "Generation and analysis of 280,000 human expressed sequence tags", Genome Research (1996), vol. 6, No. 9, p. 807–828.

* cited by examiner

Primary Examiner—Lorraine Spector
Assistant Examiner—Sandra Wegert
(74) Attorney, Agent, or Firm—Edwards & Angell, LLP; Peter F. Corless; Christine C. O'Day (57) ABSTRACT

A novel organic anion transporter gene participating in organic anion transport in the placenta; and an organic anion transporter which is a polypeptide encoded by the gene. A placental organic anion transporter OAT4, more particularly, a placental organic anion transporter OAT4 having the amino acid sequence represented by SEQ ID NO:2 or an amino acid sequence derived therefrom by deletion, substitution or addition of a part of the amino acids thereof. A nucleic acid (preferably DNA) having a base sequence encoding the placental organic anion transporter OAT4 or a base sequence hybridizable therewith under stringent conditions.

2 Claims, 6 Drawing Sheets

PLACENTAL ORGANIC ANION TRANSPORTER

This application is a 371 of PCT/JP00/03878, filed Jun. 15, 2000, which claims priority to Japanese Patent Application No. 11-187244, filed Jul. 1, 1999.

TECHNICAL FIELD

The present invention relates to gene participating in an organic anion (organic negatively-charged ion) transport and to a polypeptide for which the gene codes. More particularly, the present invention relates to an organic anion transporter OAT4 of a placenta type, to gene coding therefor, to a probe for detecting the gene and to an antibody which is able to recognize the protein.

BACKGROUND OF THE INVENTION

Kidney and liver play an important role in metabolism and excretion of xenobiotics and pharmaceuticals. Urinary tubule cells of kidney are epithelial cells having a polarity and contact the blood via a basolateral membrane to carry out transfer of various substances. It has been predicted from the physiological studies up to now that a part of the organic ion is incorporated into kidney by a transport carrier (transporter) via a basolateral membrane and also that an organic anion produced by metabolism in cells is excreted by the transporter.

Since organic anion contains pharmaceuticals and environmental toxins or many of metabolites thereof, an organic anion transport system has been widely known as a xenobiotics excretion system or a pharmaceuticals transport system as well.

Incorporation of an organic anion by urinary tubule cells has been studied by an experimental system using an isolated organ perfusion method, an isolated cell membrane vesicle system, etc. However, according to the conventional means, it is difficult to analyze the organic anion transport system via basolateral membrane in detail and there has been a demand that the transporter per se is isolated and analyzed.

Organic anion transport is also carried out in the tissues other than kidney and liver. Placenta is a tissue where material exchange is actively carried out between fetus and the mother's body and the substances necessary for living organism including saccharides and amino acids are efficiently transported to fetus from the mother's body via a transporter.

On the other hand, placenta also plays a role as a tissue barrier for fetus against the external environment. Placenta shows a certain type of limitation to a free transfer of the xenobiotics ingested by mother's body to the fetus and a part of such a function is thought to be by a removal of the xenobiotics from a fetus circulation by a xenobiotic excretion transporter.

In addition, various metabolic reactions also take place even in the body of the fetus and, as a result, an organic anion is generated. Due to an anatomical specificity of the fetus, most of excretion of such metabolites is done via placenta. It is rational to conclude that an organic anion transporter is present in placenta and plays such a role.

As such, it is believed that the transport of xenobiotics (particularly, transport of organic anion) in placenta plays an important role for the growth and the genetic toxicity of fetus. However, details of the transfer therein have been unknown than that in kidney and liver.

The present inventors have isolated and reported on an organic anion transporter OAT1 (*J. Biol. Chem.*, volume 272, pages 18526–18529, 1997), OAT2 (*FEBS Letter*, 429, pages 179–182, 1998) and OAT 3 (*J. Biol. Chem.*, volume 274, pages 13675–13680, 1999) which play a central role in kidney, liver, brain, etc. Patent applications for them have been also filed already. OAT1, OAT2 and OAT3 are the transporters which are able to transport many organic anions having different chemical structures and they carry out the transport of various anionic pharmaceuticals as well.

Isolation and identification of OAT1, OAT2 and OAT3 show that organic anion transporters form a family. Members of this family have been known to be expressed not only in organs such as kidney and liver which play a central role in external excretion of xenobiotics but also in brain which forms a tissue barrier.

From those facts, the present inventors have predicted the presence of an organic anion transporter in placenta as a functional unit of the tissue barrier and as a route for excretion of metabolites of fetus and have isolated a novel organic anion transporter existing in placenta.

DISCLOSURE OF THE INVENTION

An object of the present invention is to identify and to provide a novel organic anion transporter gene participating in an organic anion transport in placenta and also an organic anion transporter which is a polypeptide for which the gene codes. Other objects are obvious from the following descriptions.

DESCRIPTION OF THE PREFERRED EMBODIMENTS

As mentioned already, the present inventors have isolated three organic anion transporters—OAT1, OAT2 and OAT3. They have a homology in an amino acid sequence to an extent of around 40% each other. Based upon such sequences, an EST database (expressed sequence tag database) was retrieved and a novel cDNA having a homology to OAT 1, 2 and 3 was identified. Using this cDNA fragment, a novel clone (OAT4) which has not been report yet was identified from a human kidney cDNA library and confirmed to be a placenta type.

Accordingly, the present invention relates to an organic anion transporter OAT4 of a placenta type and, more particularly, it relates to an organic anion transporter OAT4 of a placenta type having an amino acid sequence of SEQ ID NO:2 of the Sequence Listing or having an amino acid sequence where a part of the amino acids may be deleted and other amino acid(s) may be substituted therewith or added thereto.

The organic anion transporter OAT4 of a placenta type according to the present invention is an organic anion transporter OAT4 of a placenta type which has an ability of incorporating an organic anion such as estrone sulfate, dehydroepiandrosterone sulfate and/or ochratoxin A.

The present invention also relates to a nucleic acid or, preferably, DNA which has a base sequence coding for protein having an amino acid sequence of SEQ ID NO:2 of the Sequence Listing or having an amino acid sequence where a part of the amino acids may be deleted and other amino acid(s) may be substituted therewith or added thereto or has a base sequence being able to hybridize therewith under a stringent condition. It also relates to gene which codes for the above-mentioned anion transporter OAT4 of a placenta type of the present invention.

The present invention further relates to a nucleic acid or, preferably, DNA which has a base sequence comprising at least continuous 14 bases or, preferably, at least continuous 20 bases of the DNA having the base sequence shown by SEQ ID NO:1 of the Sequence Listing or a complementary chain thereof The nucleic acid such as the said DNA is useful as a probe for the detection, identification or quantitative determination of the gene coding for the above-mentioned organic anion transporter OAT4 of a placenta type of the present invention.

The present invention furthermore relates to an antibody which is able to recognize the above-mentioned organic anion transporter OAT4 of a placenta type of the present invention.

The organic anion transporter OAT4 of the present invention is a transporter which has a substrate selectivity of a broad range having an ability of transporting (incorporating) an organic anion having a different chemical structure. The organic anion transporter OAT4 of a placenta type of the present invention has an ability of incorporating an organic anion such as estrone sulfate, dehydroepiandrosterone sulfate and/or ochratoxin A.

The present inventors have retrieved a EST database which has been laid-open to the public based upon a base sequence information for OAT1, OAT2 and OAT3 which were already isolated by the present inventors whereupon they have obtained a novel cDNA fragment H12876 having a homology to OAT1, OAT2 and OAT3. Using a probe where this H12876 was labeled with $^{32}$p, the present inventors screened a human kidney cDNA library which was constituted already.

As a result, a novel cDNA (hOAT4 cDNA) having an organic anion transporting activity was obtained. Determination of the base sequence of the resulting cDNA (OAT4 cDNA) was carried out by an automatic sequencer (manufactured by Applied Biosystems) using a specific primer and found to have a base sequence shown in SEQ ID NO:1 of the Sequence Listing.

In order to confirm that the resulting OTA4 has an organic anion transport activity, cRNA (an RNA complementary to cDNA) was prepared from a plasmid containing this cDNA according to a method of Sekine, et al. (Sekine, T., et al., *J. Biol. Chem.*, volume 272, pages 18526–18529, 1997) and injected into oocytes of *Xenopus laevis* and the oocytes were subjected to an incorporation experiment for various organic anions and organic cations which were labeled with radio-isotopes.

Figure 1:
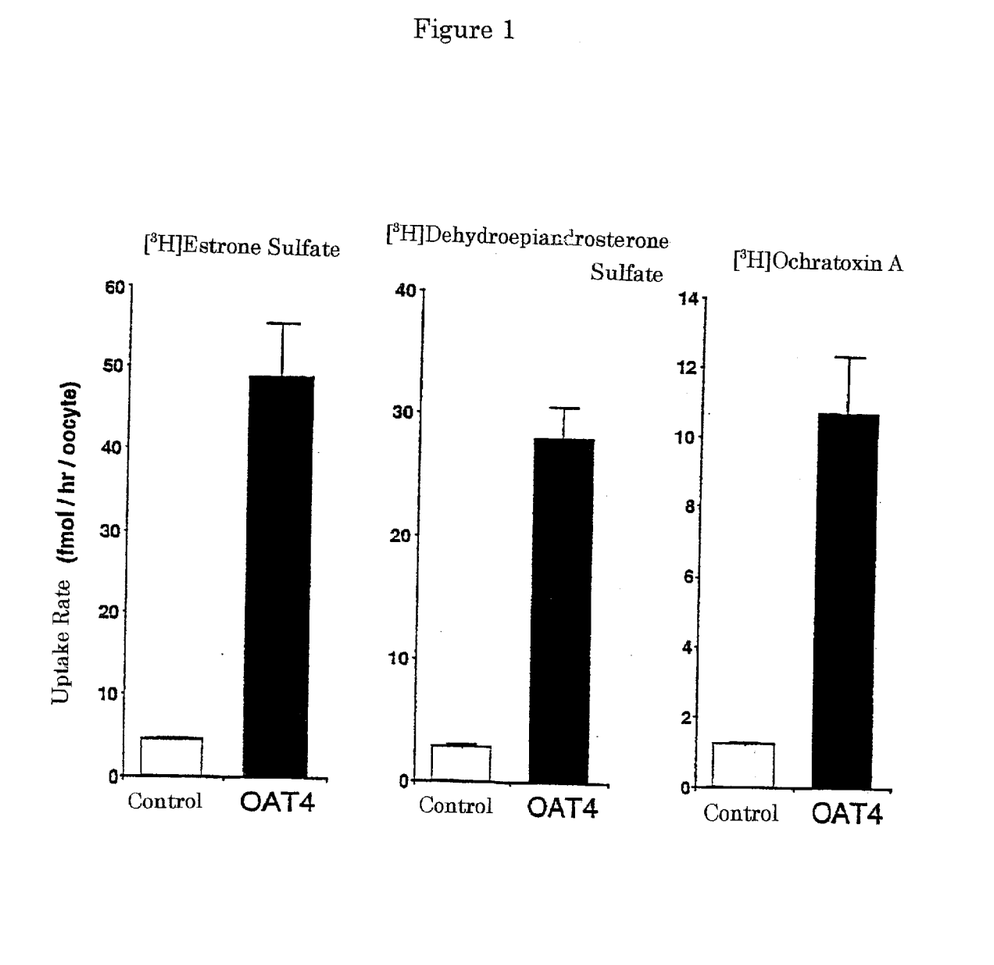
FIG. 1 shows an organic anion incorporating activity when OAT4 of the present invention is expressed in oocytes of *Xenopus laevis*.

The result is shown in FIG. 1. As shown in FIG. 1, it was found that the oocytes expressing the OAT4 incorporated $^{3}$H-estrone sulfate, $^{3}$H-dehydroepiandrosterone sulfate and $^{3}$H-ochratoxin A. On the contrary, no incorporation was noted for $^{14}$C-TEA (tetraethylammonium) which is a typical organic cation.

After that, the above-mentioned oocytes into which OAT4 cRNA was injected was used for checking the changes in the amount of estrone sulfate, dehydroepiandrosterone sulfate and ochratoxin A incorporated by OAT4 of the present invention at various concentrations whereby a Michaelis-Menten dynamic test for an organic anion transport was carried out.

Figure 2:
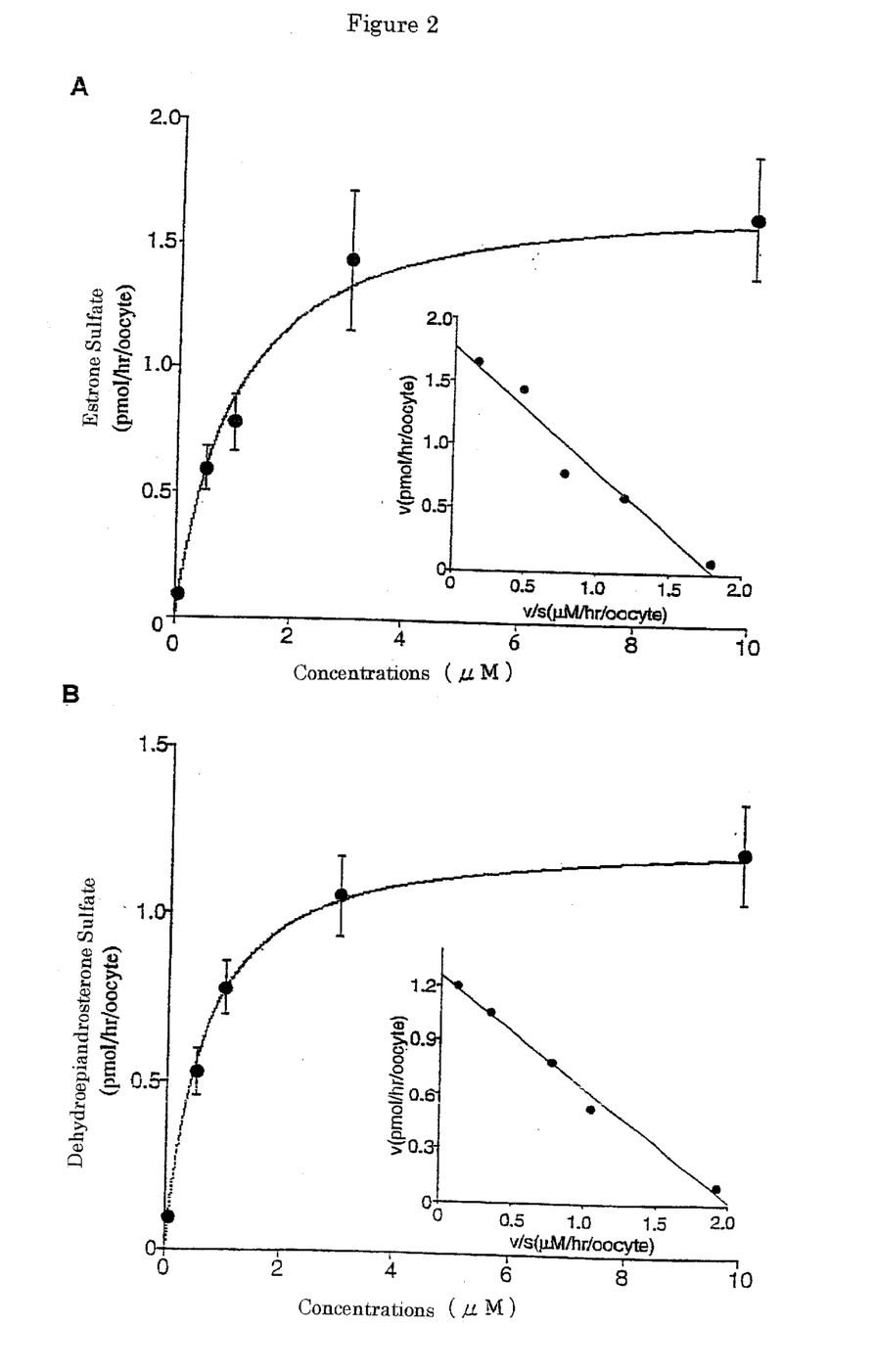
FIG. 2 shows the result of a dynamic test of transport of A) estrone sulfate and B) dehydroepiandrosterone sulfate using the oocytes in which OAT4 of the present invention is expressed.

The result is shown in FIG. 2. As a result, it was found that the OAT4 of the present invention increased the incorporated amount of the organic anion dependently of the concentration. The Km values of estrone sulfate and dehydroepiandrosterone sulfate were found to be 1.01±0.15 $\mu$M and 0.63±0.04 $\mu$M, respectively.

Figure 3:
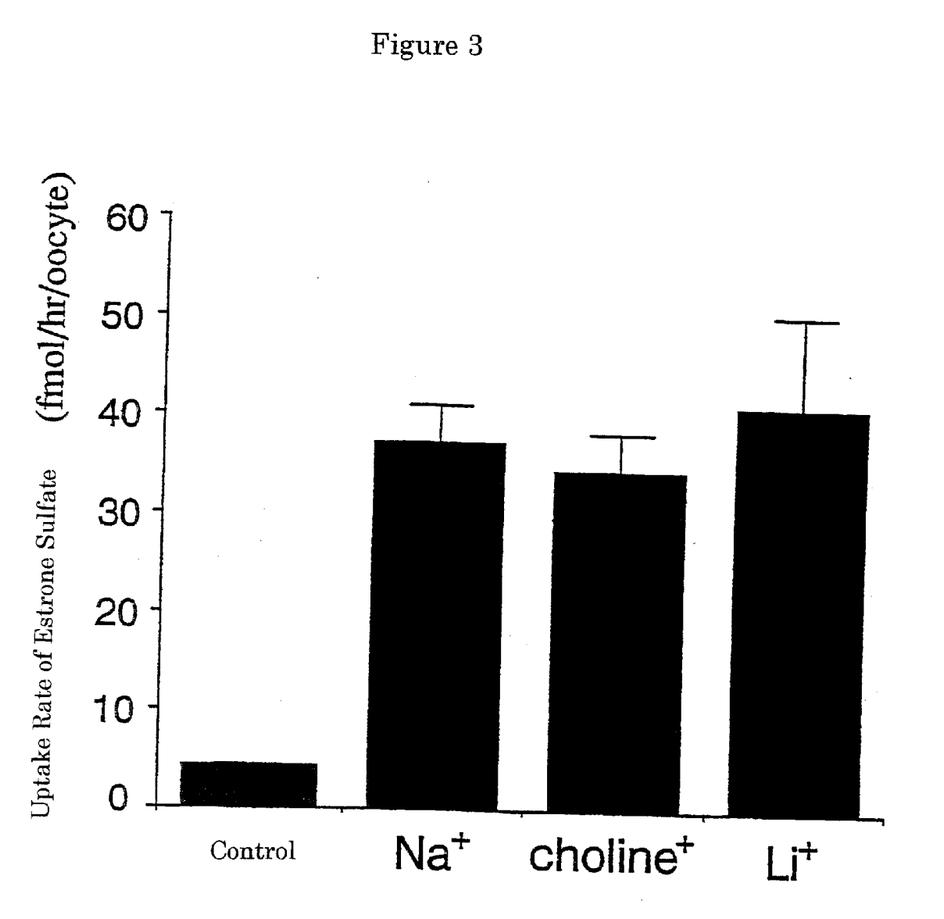
FIG. 3 shows the affection by the presence of various cations in the transport of estrone sulfate using the oocytes in which OAT4 of the present invention is expressed.

Dependency of the OAT4 of the present invention on sodium in an organic anion transport was investigated. Incorporation of estrone sulfate by OAT4 was tested in the presence of various extracellular cations. The result is shown in FIG. 3. As shown in FIG. 3, an incorporation activity of estrone sulfate via OAT4 was noted when sodium ion, choline ion and lithium ion are present as an extracellular ion and, even when the extracellular sodium is substituted with lithium and choline, there was no change in the transport of estrone sulfate via OAT4 whereupon it was clarified that OAT4 is an organic anion transporter which was independent upon the extracellular sodium.

Further, in order to investigate the substrate selectivity of OAT4 of the present invention, various ionic substances were added to an incorporation experimental system of $^{3}$H-estrone sulfate and the influence thereby was tested (Inhibition Experiment).

Figure 4:
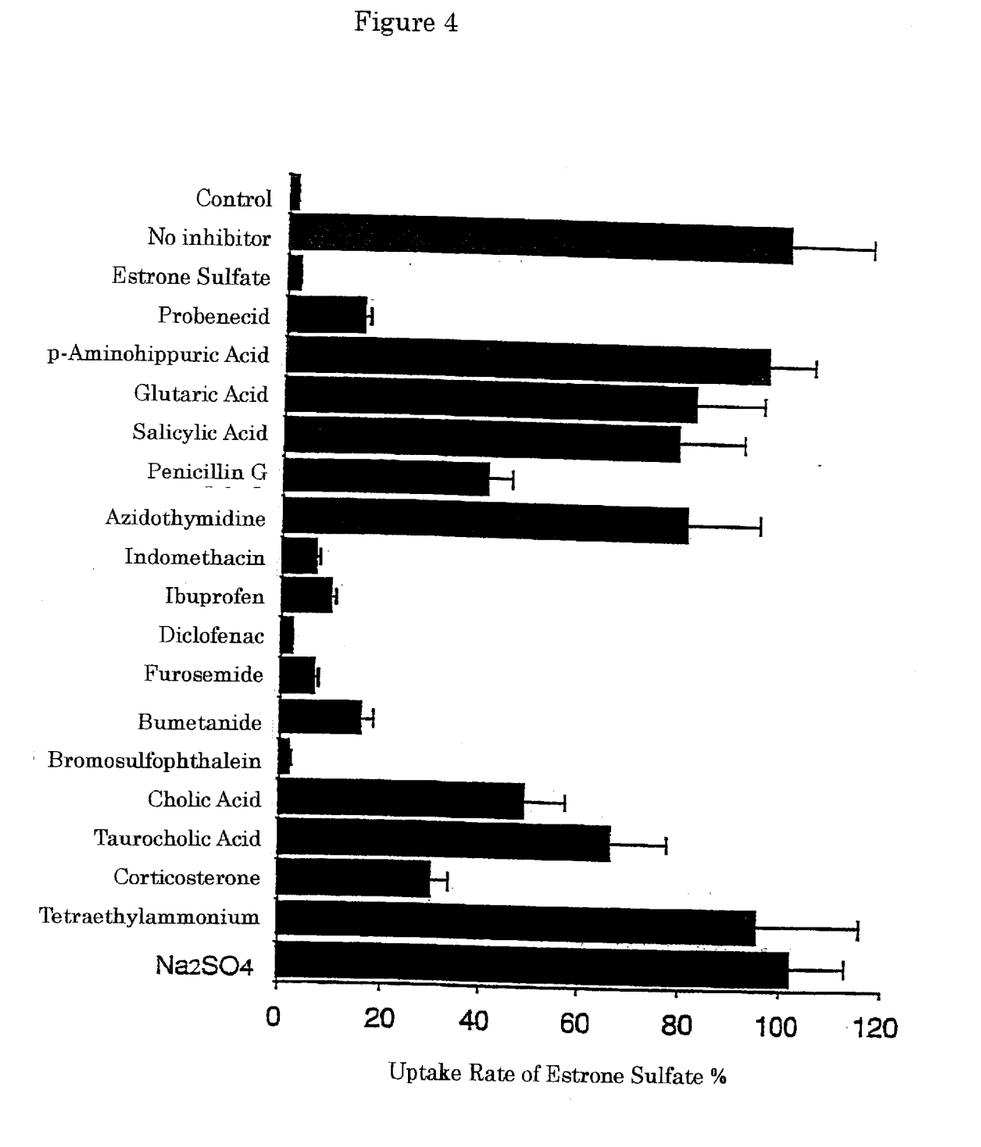
FIG. 4 shows the result of the transport inhibition test of various organic substances in an organic anion transport of OAT4 of the present invention.

The result is shown in FIG. 4. As a result, various anionic substances (such as probenecid, penicillin G, indomethacin, ibuprofen, diclofenac, furosemide, bumetanide, bromosulfophthalein, cholic acid and taurocholic acid) significantly inhibited the transport of $^{3}$H-estrone sulfate by OAT4 but cationic substances such as tetraethylammonium and inorganic sulfates did not show an inhibiting action. From the above result, it was clarified that OAT4 was a multi-selective organic anion transporter.

Figure 5:
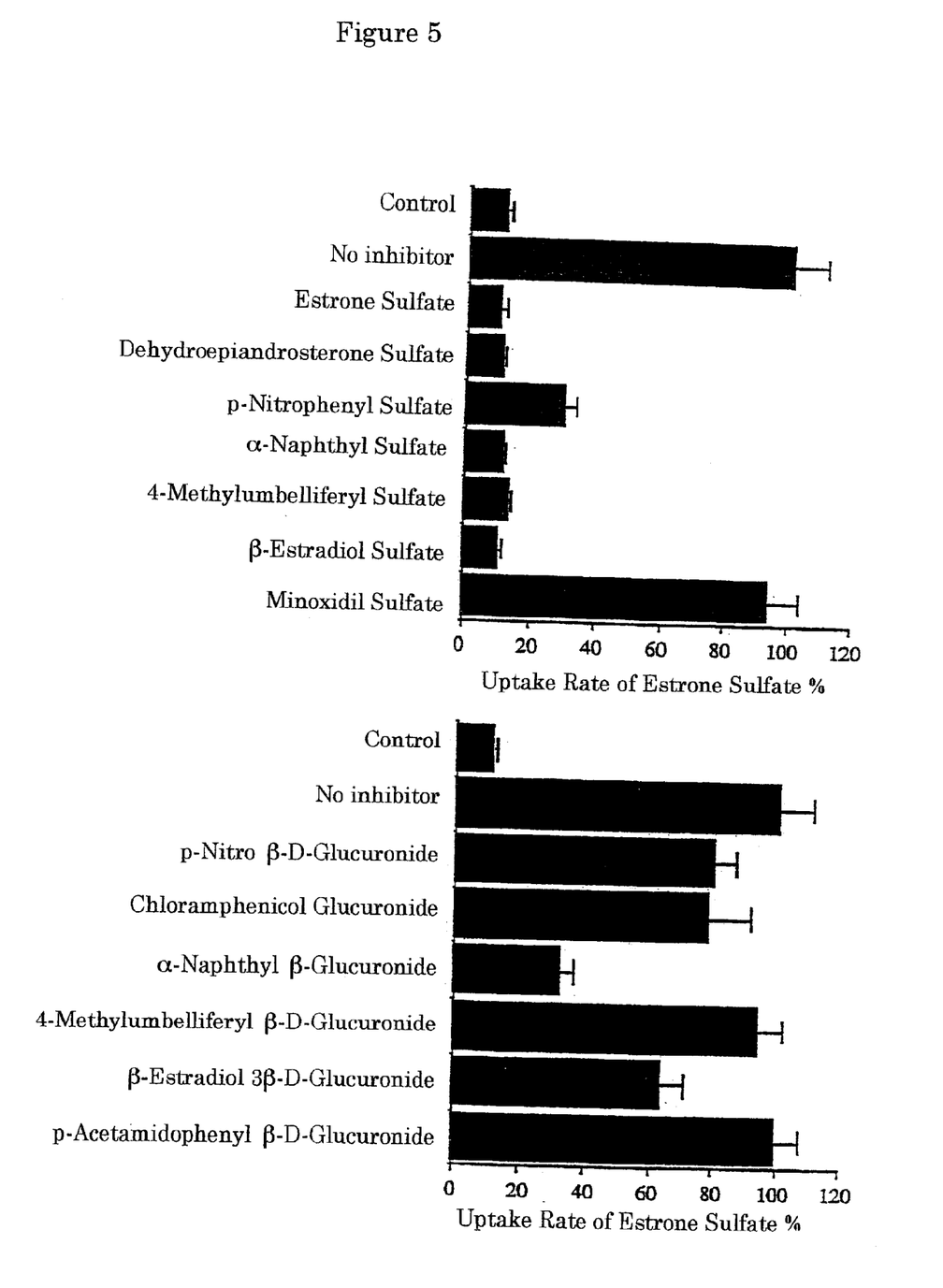
FIG. 5 shows the result of the transport inhibition test of OAT4 by various sulfate conjugates and glucuronic acid conjugates.

Since OAT4 of the present invention showed an incorporation activity for conjugates of the two sulfates, i.e. estrone sulfate and dehydroepiandrosterone sulfate, an inhibiting experiment was carried out to check whether various sulfate conjugates and glucuronate conjugates show an interaction with OAT4. The result is shown in FIG. 5. As a result, all sulfate conjugates except minoxidil sulfate showed an interaction with OAT4. On the contrary, glucuronate conjugates showed only a weak interaction with OAT4 except α-naphthyl-β-glucuronide.

Then, a northern blot analysis was carried out to investigate in which site of human tissues the OATA4 of the present is expressed.

Figure 6:
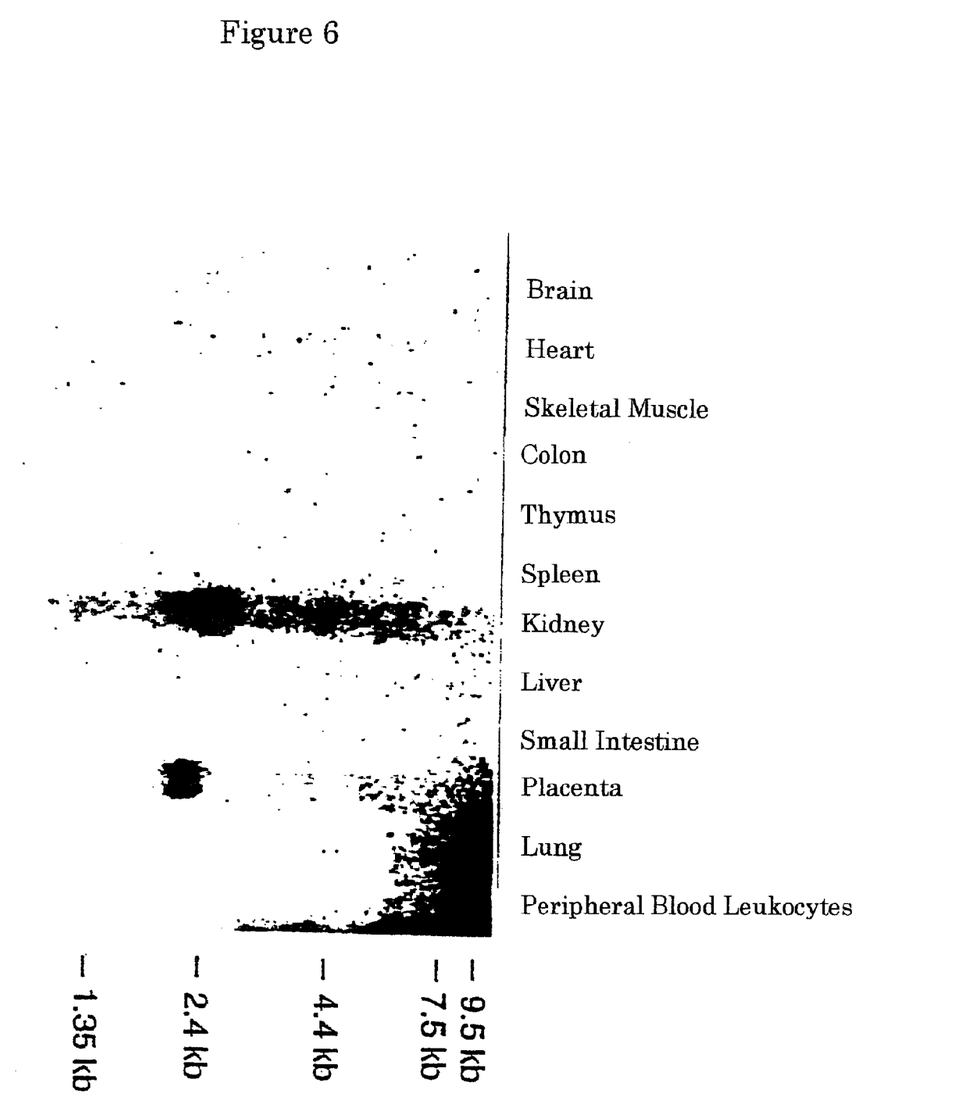
FIG. 6 a photographic picture showing the result of the northern blotting analysis of the OAT4 gene of the present invention.

Result of the northern blotting is shown in FIG. 6. As a result, it was found that a strong band was detected in kidney and placenta only in the OAT4 of the present invention and accordingly that the OAT4 of the present invention was a placenta type.

Accordingly, the OAT4 of the present invention is an organic anion transporter of a human placenta type and, in the present invention, that is called an organic anion transporter OAT4 of a placenta type.

With regard to the protein of the present invention, in addition to that which has an amino acid sequence shown by SEQ ID NO:2, those in which one or more amino acid(s) in the amino acid sequence shown by SEQ ID NO:2 is/are deleted, substituted or added may be exemplified. Deletion, substitution or addition of amino acid(s) may be within such an extent that an organic anion transport activity is not lost and the number(s) is/are usually 1 to about 110 or, preferably, from 1 to about 55 amino acid(s). Such an amino acid has a homology in terms of an amino acid sequence to the amino acid sequence shown by SEQ ID NO:2 to an extent of usually by 75% or, preferably, by 90%.

In the present invention, hybridization under a stringent condition is usually carried out in such a manner that hybridization is conducted in a hybridization solution of 5×SSC or similar salt concentration thereto at the temperature condition of 37–42° C. for about 12 hours, a preliminary washing is conducted with a solution of 5×SSC or similar salt concentration thereto and then a washing is conducted with a solution of 1×SSC or similar salt concentration thereto. In order to achieve a higher stringency, it can be done where a washing is conducted in a solution of 0.1×SSC or similar salt concentration thereto.

Nucleic acid which can be subjected to a hybridization in a stringent condition in the present invention includes that which can be subjected to a hybridization under the above-mentioned conditions.

It is also possible that the organic anion transporter and gene thereof according to the present invention is isolated and obtained by means of a screening where tissues or cells of appropriate mammal besides human being are used as a gene source. With regard to the mammal, non-human animals such as dogs, cattle, horses, goats, sheep, monkeys, pigs, rabbits, rats and mice may be used. Screening and isolation of the gene may be advantageously carried out by means of a homology screening, a PCR screening, etc.

As to the resulting cDNA, its base sequence is determined by a conventional method and a translated region is analyzed whereby the protein coded therefor or the amino acid sequence of OAT4 can be determined.

The fact that the resulting cDNA is a cDNA of an organic anion transporter or, in other words, the gene product coded for cDNA is an organic anion transporter can, for example, be inspected as follows. Thus, cRNA prepared from the resulting OAT4 cDNA is introduced into oocytes to express and an ability of transporting (incorporating) the organic anion into cells can be confirmed by measuring the expression of the substrate into the cells by means of a conventional expression experiment (Sekine, et al., *J. Biol. Chem.*, volume 272, pages 18526–18529, 1997) using an appropriate anion as a substrate.

It is also possible that the expression experiment which is as same as in the above-mentioned expressed cells is applied to investigate the transport characteristic and the substrate specificity of OAT4.

When an appropriate cDNA library or genomic DNA library prepared from a different genetic source is screened using the OAT4 cDNA, it is possible to isolate homologous gene, chromosomal gene, etc. derived from different tissues and different living bodies.

It is further possible to isolate the gene from a cDNA library by a conventional PCR method using a synthetic primer designed based on the information of the disclosed base sequence (or a part of it) shown in the base sequence (SEQ ID NO:1) of the gene of the present invention.

The DNA library such as a cDNA library and a genomic DNA library can be prepared by a method mentioned, for example, in *Molecular Cloning* by Sambrook, J., Fritsh, E. F. and Maniatis, T., published by Cold Spring Harbor Laboratory Press, 1989. When a library is commercially available, that may be used as well.

The organic anion transporter (OAT4) of the present invention may be produced, for example, by means of a gene recombination technique using cDNA coding for the organic anion transporter. For example, DNA (cDNA or the like) coding for the organic anion transporter is incorporated into an appropriate expression vector and the resulting recombinant DNA can be introduced into an appropriate host cell. Examples of the expression system (host vector system) for the production of a polypeptide are expression systems of bacteria, yeast, insect cells and mammalian cells. In order to obtain a functional protein among them, it is desirable to use insect cells and mammalian cells.

For example, in order to express a polypeptide in mammal, DNA coding for an organic anion transporter is inserted into a downstream to an appropriate promoter (such as SV40 promoter, LTR promoter and elongation 1α promoter) in an appropriate expression vector (such as vector of a retrovirus, papilloma virus, vaccinia virus vector and vector of an SV40 type) whereupon an expression vector is constructed. Then appropriate animal cells are subjected to a transformation using the resulting expression vector and the transformant is incubated in an appropriate medium to give a desired polypeptide. Examples of the mammal cells used as a host are cell strains including simian COS-7 cells, Chinese hamster CHO cells, human Hela cells, primary culture cells derived from kidney tissues, LLC-PK1 cells derived from kidney of pig, OK cells derived from opossum kidney, etc.

With regard to cDNA which codes for an organic anion transporter OAT4, the cDNA having a base sequence shown in SEQ ID NO: 1 may be used for example and, in addition, it is not limited to the above-mentioned cDNA but DNA corresponding to the amino acid sequence is designed and the DNA coding for the polypeptide may be used. In that case, 1–6 kind(s) of codon has/have been known for coding for each amino acid and, although any codon may be selected for use, a sequence having higher expression can be designed when, for example, frequent use of codon by the host utilized in the expression is taken into consideration. Like in the case of chemical synthesis of DNA and fragmentation of the above cDNA, the DNA having a designed base sequence can be prepared, for example, by means of a partial modification of the base sequence. Artificial partial modification of and introduction of variation into a base sequence can be carried out by a site-directed mutagenesis (Mark, D. F., et al: *Proc. Natl. Acad. Sci. USA*, volume 18, pages 5662–5666, 1984), etc. utilizing a primer comprising a synthetic oligonucleotide coding for the desired modification.

The nucleotide (oligonucleotide or polynucleotide) which hybridizes to the organic anion transporter gene of the present invention under a stringent condition can be used as a probe for detecting the organic anion transporter gene and, moreover, it can be used as antisense oligonucleotide, ribozyme, decoy, etc. for modulation of expression of the organic anion transporter. With regard to such a nucleotide, a nucleotide containing a partial sequence of usually not less than continuous 14 bases in the base sequence shown by SEQ ID NO:1 or a complementary sequence thereof may be used for example and, in order to hybridize more specifically, longer sequence such as not less than 20 bases or not less than 30 bases may be used as a partial sequence.

It is also possible that the organic anion transporter of the present invention or a polypeptide having the immunological homology thereto is used to obtain an antibody thereto and the antibody is able to be utilized for detection, purification, etc. of the organic anion transporter. The antibody can be manufactured using the organic anion transporter of the present invention or a fragment thereof or a synthetic peptide having a partial sequence thereof as an antigen. Polyclonal antibody can be manufactured by a conventional method in which an antigen is inoculated to a host animal (such as rat and rabbit) and immune serum is obtained while monoclonal antibody can be manufactured by a conventional way such as a hybridoma method.

EXAMPLES

The present invention will now be further illustrated by way of the following Examples although those Examples do not limit the present invention.

In the following Examples, each operation is carried out, unless otherwise mentioned, by a method mentioned in *Molecular Cloning* by Sambrook, J., Fritsh, E. F. and Maniatis, T., published by Cold Spring Harbor Laboratory Press, 1989 or according to the direction for use of the commercially available product when commercially available kit is used.

Example 1

Isolation of Multi-Specific Organic Anion Transporter 4 (OAT4) cDNA and Analysis Thereof.

An laid-open EST database was investigated based upon a base sequence information of OAT1, OAT2 and OAT3 which were isolated by the present inventors already. As a result, a novel cDNA fragment 12876 having a homology with OAT1, OAT2 and OAT3 was obtained.

A human kidney cDNA library which was constructed already was screened using a probe where the resulting H12876 was labeled with $^{32}$p. A hybridization was carried out for one night and day in a solution for hybridization at 37° C. and, after that, the filter membrane was washed with a 0.1×SSC/0.1% SDS at 37° C. As to the hybridization solution, a buffer of pH 6.5 containing 50% formamide, 5×standard saline citrate (SSC), 3×Denhardt's solution, 0.2% SDS, 10% dextran sulfate, 0.2 mg/ml modified salmon semen DNA, 2.5 mM sodium pyrophosphate, 25 mM MES and 0.01% Antifoam B (manufactured by Sigma) was used.

Clone which was isolated into λ Zip Lox was further subjected to a subcloning to a plasmid vector pZL by an in vivo excision method. As a result, a novel cDNA (hOAT4 cDNA) having an organic anion transporting activity was prepared.

Determination of a base sequence of the above-prepared cDNA (OAT4 cDNA) was carried out by an automatic sequencer (manufactured by Applied Biosystems) using a specific primer. The base sequence is shown in SEQ ID NO:1 of the Sequence Listing.

Example 2

Characterization of OAT4 Function.

From an OAT4 cDNA-containing plasmid was prepared cRNA (an RNA complementary to cDNA) in vitro using a T7 RNA polymerase (Sekine, T., et al., *J. Biol. Chem.*, volume 272, pages 18526–18529, 1997).

The resulting cRNA was injected into oocytes of *Xenopus laevis* according to the already-reported method (Sekine, T., et al., *J Biol. Chem.*, volume 272, pages 18526–18529, 1997) and the oocytes were subjected to an incorporation experiment using various labeled organic anions and organic cations. As a result, it was found as shown in FIG. 1 that the oocytes in which OAT4 was expressed showed incorporation of $^3$H-estrone sulfate, $^3$H-dehydroepiandrosterone sulfate and $^3$H-ochratoxin A. On the contrary, uptake of $^{14}$C-TEA (tetraethylammonium) which is a typical organic cation was not noted.

Example 3

Kinetic Test of OAT4 for Organic Anion Transport.

A Michaelis-Menten dynamic test was carried out for an organic anion transport of OAT4. Changes in the uptake amount of various concentrations of estrone sulfate and dehydroepiandrosterone sulfate by OAT4 were tested whereby concentration dependency of those substrates by OAT4 was investigated. The uptake experiment of labeled estrone sulfate and dehydroepiandrosterone sulfate was carried out according to the above-mentioned method using oocytes into which OAT4 cRNA was injected.

As a result, the Km values of estrone sulfate and dehydroepiandrosterone sulfate were 1.01±0.15 $\mu$M and 0.63±0.04 $\mu$M, respectively (refer to FIG. 2).

Example 4

Test on Cation-Dependency in Organic Anion Transport of OAT4.

Sodium-dependency of OAT4 in an organic anion transport was investigated. Even when extracellular sodium was substituted with lithium and choline, there was no change in the transport of estrone sulfate via OAT4 and it was clarified that OAT4 is an organic anion transporter which is independent on extracellular sodium (refer to FIG. 3).

In order to further investigate the substrate selectivity of OAT4, various anionic substances were added to a system in an uptake experiment system of $^3$H-estrone sulfate in oocytes into which OAT4 cRNA was injected and the influence was investigated (inhibition experiment). An uptake experiment of $^3$H-estrone sulfate was carried out according to the above-mentioned method using oocytes into which OAT4 cRNA was injected. Uptake of 50 nM $^3$H-estrone sulfate was measured in the presence and absence of 500 $\mu$M of various compounds (unlabeled). The result was that various anionic substances (such as probenecid, penicillin G, indomethacin, ibuprofen, diclofenac, furosemide, bumetanide, bromosulfophthalein, cholic acid and taurocholic acid) significantly inhibited the transport of $^3$H-estrone sulfate by OAT4 (refer to FIG. 3). On the other hand, cationic substances such as tetraethylammonium and inorganic sulfates did not show any inhibiting action (refer to FIG. 4). From the above results, it was clarified that OAT4 is a multi-specific organic anion transporter.

Example 5

Uptake Test of Various Sulfate Conjugates and Glucuronic Acid Conjugates by OAT4.

OAT4 showed an uptake activity for conjugates of the two sulfate—estrone sulfate and dehydroepiandrosterone sulfate—and, therefore, an inhibitory test was carried out to see whether various sulfate conjugates and glucuronic acid conjugates also show an interaction with OAT4. As shown in FIG. 5, all sulfate conjugates except minoxidil sulfate showed an interaction with OAT4. On the contrary, glucuronic acid conjugates showed only weak interaction with OAT4 except α-naphthyl-β-glucuronide.

Example 6

Northern Blotting Analysis of OAT4 Gene.

Analysis of expression (northern blotting) of OAT4 gene in various tissues of human being was carried out. Full length of OAT4 cDNA was labeled with $^{32}$p-dCTP and this was used as a probe for carrying out a hybridization of a filter (manufactured by Clonetec) where RNA extracted from various tissues of human being was blotted. Hybridization was carried out overnight using a hybridization solution containing the full length of OAT4 cDNA and the filter was washed at 65° C. with a 0.1×SSC containing 0.1% SDS. As a result of northern blotting, a strong band was detected only in the cases of kidney and placenta (refer to FIG. 6). Incidentally, the blots in FIG. 6 shows brain, heart, skeletal muscle, colon, thymus, spleen, kidney, liver, small intestine, placenta, lung and peripheral blood leukocytes from left to right.

Industrial Applicability

The present invention provides a novel organic anion transporter OAT4 of a placenta type and also a gene coding therefor. A transporter is a protein which incorporates or excretes a substance necessary for the maintenance of life of cells as same as a channel and its abnormality causes various diseases. Particularly, the organic anion transporter OAT4 of a placenta type according to the present invention is selectively expressed in kidney and placenta and its clarification is useful for prevention and treatment of various renal diseases and abnormal growth of fetus.

What is claimed is:

1. The isolated organic anion transporter OAT4 of a placenta type, wherein it has an amino acid sequence of SEQ ID NO: 2 of the Sequence listing.

2. The isolated organic anion transporter OAT4 of a placenta type according to claim 1 wherein it has an ability of transporting estrone sulfate, dehydroepiandrosterone sulfate and/or ochratoxin A.

* * * * *

SEQUENCE LISTING

<160> NUMBER OF SEQ ID NOS: 2

<210> SEQ ID NO 1
<211> LENGTH: 2210
<212> TYPE: DNA
<213> ORGANISM: Human

<400> SEQUENCE: 1

```
gttccaaaca gcagttaggt cagcagtccg ctcagccgag gcagctctgt tcatggcgtt      60
ctcgaagctc ttggagcaag ccggaggcgt gggcctcttc cagaccctgc aggtgctcac     120
cttcatcctc ccctgcctca tgataccttc ccagatgctc ctggagaact tctcagccgc     180
catcccaggc caccgatgct ggacacacat gctggacaat ggctctgcgg tttccacaaa     240
catgaccccc aaggcccttc tgaccatctc catcccgcca ggcccaacc aggggcccca     300 ccagtgccgc cgcttccgcc agccacagtg gcagctcttg gacccaatg ccacggccac     360 cagctggagc gaagctgaca cggagccgtg tgtgacggc tgggtctatg accgcagcgt     420
cttcacctcc accatcgtgg ccaagtggga cctggtgtgc agctcccagg gcttgaagcc     480
cctaagccag tccatcttca tgtccgggat cctggtgggc tcctttatct ggggcctcct     540
ctcctaccgg tttgggagga agccgatgct gagctggtgc tgcctgcagt tggccgtggc     600
gggcaccagc accatcttcg ccccaacatt cgtcatctac tgcggcctgc ggttcgtggc     660
cgcttttggg atggccggca tctttctgag ttcactgaca ctgatggtgg agtggaccac     720
gaccagcagg agggcggtca ccatgacggt ggtgggatgt gccttcagcg caggccaggc     780
ggcgctgggc ggcctggcct ttgccctgcg ggactggagg actctccagc tggcagcatc     840
agtgcccttc tttgccatct ccctgatatc ctggtggctg ccagaatccg cccggtggct     900
gattattaag ggcaaaccag accaagcact tcaggagctc agaaaggtgg ccaggataaa     960
tggccacaag gaggccaaga acctgaccat agaggtgctg atgtccagcg tgaaggagga    1020
ggtggcctct gcaaaggagc cgcggtcggt gctgacctg ttctgcgtgc ccgtgctccg    1080
ctggaggagc tgcgccatgc tggtggtgaa tttctctcta ttgatctcct actatgggct    1140
ggtcttcgac ctgcagagcc tgggccgtga catcttcctc ctccaggccc tcttcgggcc    1200
cgtggacttc ctgggccggg ccaccactgc cctcttgctc agtttccttg gccgccgcac    1260
catccaggcg ggttcccagg ccatggccgg cctcgccatt ctagccaaca tgctggtgcc    1320
```

-continued

```
gcaagatttgc agaccctgc gtgtggtctt tgctgtgctg ggaaagggat gttttgggat    1380 aagcctaacct gcctcacca tctacaaggc tgaactcttt ccaacgccag tgcggatgac    1440 agcagatggca ttctgcata cagtgggccg gctgggggct atgatgggtc ccctgatcct    1500 gatgagccgcc aagccctgc ccctgctgcc tcctctcctc tatggcgtta tctccattgc    1560 ttccagcctgg ttgtgctgt tcttcctccc ggagacccag ggacttccgc tccctgacac    1620 tatccaggacc tggagagcc agaaatcaac agcagcccag ggcaaccggc aagaggccgt    1680 cactgtggaaa gtacctcgc tctagaaatt gtgcctgcat ggagccccct tagtcaaaga    1740
ctcctggaaa ggagttgcct cttctccaat cagagcgtgg aggcgagttg ggcgacttca    1800
agggcctggc atggcagagg ccaggcagcc gtggccgagt ggacagcgtg gccgtctgct    1860
gtggctgaag gcagcttcca cagctcactc ctcttctccc tgccctgatc agattcccca    1920
ccttacccgg gccctacagg agcctgtgca gatggccatg cccaaccaat aacgagacgg    1980
ttcccctccc tttccctgcc aggctcatgt ctttacacct tcactcagcc acgccaacca    2040
gagactgggt tccaatctca ccccaccaca tacagagccc tcatctgtga aatgagaatg    2100
atcacgtgac ccacccccca gggcaggtat cagggtgaac tgatcttagc accggccaaa    2160
taaatggaac tgctgagag agctgccaga taaaaaaaaa aaaaaaaaaa                2210
```

```
<210> SEQ ID NO 2
<211> LENGTH: 550
<212> TYPE: PRT
<213> ORGANISM: Human

<400> SEQUENCE: 2

Met Ala Phe Ser Lys Leu Leu Glu Gln Ala Gly Gly Val Gly Leu Phe
  1               5                  10                  15

Gln Thr Leu Gln Val Leu Thr Phe Ile Leu Pro Cys Leu Met Ile Pro
             20                  25                  30

Ser Gln Met Leu Leu Glu Asn Phe Ser Ala Ala Ile Pro Gly His Arg
         35                  40                  45

Cys Trp Thr His Met Leu Asp Asn Gly Ser Ala Val Ser Thr Asn Met
     50                  55                  60

Thr Pro Lys Ala Leu Leu Thr Ile Ser Ile Pro Pro Gly Pro Asn Gln
 65                  70                  75                  80

Gly Pro His Gln Cys Arg Arg Phe Arg Gln Pro Gln Trp Gln Leu Leu
                 85                  90                  95

Asp Pro Asn Ala Thr Ala Thr Ser Trp Ser Glu Ala Asp Thr Glu Pro
            100                 105                 110

Cys Val Asp Gly Trp Val Tyr Asp Arg Ser Val Phe Thr Ser Thr Ile
        115                 120                 125

Val Ala Lys Trp Asp Leu Val Cys Ser Ser Gln Gly Leu Lys Pro Leu
130                 135                 140

Ser Gln Ser Ile Phe Met Ser Gly Ile Leu Val Gly Ser Phe Ile Trp
145                 150                 155                 160

Gly Leu Leu Ser Tyr Arg Phe Gly Arg Lys Pro Met Leu Ser Trp Cys
                165                 170                 175

Cys Leu Gln Leu Ala Val Ala Gly Thr Ser Thr Ile Phe Ala Pro Thr
            180                 185                 190

Phe Val Ile Tyr Cys Gly Leu Arg Phe Val Ala Ala Phe Gly Met Ala
        195                 200                 205

Gly Ile Phe Leu Ser Ser Leu Thr Leu Met Val Glu Trp Thr Thr Thr
    210                 215                 220
```

-continued

```
Ser Arg Arg Ala Val Thr Met Thr Val Val Gly Cys Ala Phe Ser Ala
225                 230                 235                 240

Gly Gln Ala Ala Leu Gly Gly Leu Ala Phe Ala Leu Arg Asp Trp Arg
            245                 250                 255

Thr Leu Gln Leu Ala Ala Ser Val Pro Phe Phe Ala Ile Ser Leu Ile
            260                 265                 270

Ser Trp Trp Leu Pro Glu Ser Ala Arg Trp Leu Ile Ile Lys Gly Lys
        275                 280                 285

Pro Asp Gln Ala Leu Gln Glu Leu Arg Lys Val Ala Arg Ile Asn Gly
        290                 295                 300

His Lys Glu Ala Lys Asn Leu Thr Ile Glu Val Leu Met Ser Ser Val
305                 310                 315                 320

Lys Glu Glu Val Ala Ser Ala Lys Glu Pro Arg Ser Val Leu Asp Leu
                325                 330                 335

Phe Cys Val Pro Val Leu Arg Trp Arg Ser Cys Ala Met Leu Val Val
            340                 345                 350

Asn Phe Ser Leu Leu Ile Ser Tyr Tyr Gly Leu Val Phe Asp Leu Gln
            355                 360                 365

Ser Leu Gly Arg Asp Ile Phe Leu Leu Gln Ala Leu Phe Gly Ala Val
    370                 375                 380

Asp Phe Leu Gly Arg Ala Thr Thr Ala Leu Leu Leu Ser Phe Leu Gly
385                 390                 395                 400

Arg Arg Thr Ile Gln Ala Gly Ser Gln Ala Met Ala Gly Leu Ala Ile
                405                 410                 415

Leu Ala Asn Met Leu Val Pro Gln Asp Leu Gln Thr Leu Arg Val Val
                420                 425                 430

Phe Ala Val Leu Gly Lys Gly Cys Phe Gly Ile Ser Leu Thr Cys Leu
            435                 440                 445

Thr Ile Tyr Lys Ala Glu Leu Phe Pro Thr Pro Val Arg Met Thr Ala
    450                 455                 460

Asp Gly Ile Leu His Thr Val Gly Arg Leu Gly Ala Met Met Gly Pro
465                 470                 475                 480

Leu Ile Leu Met Ser Arg Gln Ala Leu Pro Leu Leu Pro Pro Leu Leu
                485                 490                 495

Tyr Gly Val Ile Ser Ile Ala Ser Ser Leu Val Val Leu Phe Phe Leu
            500                 505                 510

Pro Glu Thr Gln Gly Leu Pro Leu Pro Asp Thr Ile Gln Asp Leu Glu
        515                 520                 525

Ser Gln Lys Ser Thr Ala Ala Gln Gly Asn Arg Gln Glu Ala Val Thr
    530                 535                 540

Val Glu Ser Thr Ser Leu *
545                 550
```